US008704010B2

(12) United States Patent
Horton et al.

(10) Patent No.: US 8,704,010 B2
(45) Date of Patent: Apr. 22, 2014

(54) ALCOHOL PRODUCTION PROCESS WITH IMPURITY REMOVAL (75) Inventors: Trinity Horton, Houston, TX (US); Radmila Jevtic, Houston, TX (US); Victor J. Johnston, Houston, TX (US); Tianshu Pan, Houston, TX (US); Lincoln Sarager, Houston, TX (US); R. Jay Warner, Houston, TX (US); Heiko Weiner, Pasadena, TX (US); Josefina T. Chapman, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 291 days.

(21) Appl. No.: 13/094,510

(22) Filed: Apr. 26, 2011

(65) Prior Publication Data
US 2012/0010444 A1 Jan. 12, 2012

Related U.S. Application Data (60) Provisional application No. 61/332,696, filed on May 7, 2010.

(51) Int. Cl.
*C07C 27/04* (2006.01)

(52) U.S. Cl.
USPC ........................................................ 568/885

(58) Field of Classification Search
USPC ........................................................ 568/885
See application file for complete search history.

(56) References Cited

U.S. PATENT DOCUMENTS

| 2,649,407 | A | 8/1953 | Harrison et al. |
| 2,702,783 | A | 2/1955 | Harrison et al. |
| 2,744,939 | A | 5/1956 | Kennel |
| 2,882,244 | A | 4/1959 | Milton |
| 3,130,007 | A | 4/1964 | Breck |
| 3,408,267 | A | 10/1968 | Miller et al. |
| 3,445,345 | A | 5/1969 | Katzen et al. |
| 3,478,112 | A | 11/1969 | Karl et al. |
| 4,275,228 | A | 6/1981 | Gruffaz et al. |
| 4,306,942 | A | 12/1981 | Brush et al. |
| 4,317,918 | A | 3/1982 | Takano et al. |
| 4,319,058 | A | 3/1982 | Kulprathipanja et al. |
| 4,395,576 | A | 7/1983 | Kwantes et al. |
| 4,398,039 | A | 8/1983 | Pesa et al. |
| 4,421,939 | A | 12/1983 | Kiff et al. |
| 4,454,358 | A | 6/1984 | Kummer et al. |
| 4,465,854 | A | 8/1984 | Pond et al. |
| 4,471,136 | A | 9/1984 | Larkins et al. |
| 4,480,115 | A | 10/1984 | McGinnis |
| 4,492,808 | A | 1/1985 | Hagen et al. |
| 4,497,967 | A | 2/1985 | Wan |
| 4,517,391 | A | 5/1985 | Schuster et al. |
| 4,541,897 | A | 9/1985 | Sommer et al. |
| 4,615,806 | A | 10/1986 | Hilton |
| 4,626,321 | A | 12/1986 | Grethlein et al. |
| 4,678,543 | A | 7/1987 | Houben et al. |
| 4,692,218 | A | 9/1987 | Houben et al. |
| 4,777,303 | A | 10/1988 | Kitson et al. |
| 4,804,791 | A | 2/1989 | Kitson et al. |
| 4,826,795 | A | 5/1989 | Kitson et al. |
| 4,842,693 | A | 6/1989 | Wheldon |
| 4,961,826 | A | 10/1990 | Grethlein et al. |
| 4,985,572 | A | 1/1991 | Kitson et al. |
| 4,990,655 | A | 2/1991 | Kitson et al. |
| 4,994,608 | A | 2/1991 | Torrence et al. |
| 5,001,259 | A | 3/1991 | Smith et al. |
| 5,026,908 | A | 6/1991 | Smith et al. |
| 5,035,776 | A | 7/1991 | Knapp |
| 5,061,671 | A | 10/1991 | Kitson et al. |
| 5,070,016 | A | 12/1991 | Hallberg |
| 5,124,004 | A | 6/1992 | Grethlein et al. |
| 5,139,981 | A | 8/1992 | Kurland |
| 5,144,068 | A | 9/1992 | Smith et al. |
| 5,149,680 | A | 9/1992 | Kitson et al. |
| 5,185,308 | A | 2/1993 | Bartley et al. |
| 5,215,902 | A | 6/1993 | Tedder |
| 5,220,558 | A | 6/1993 | Ishikawa et al. |
| 5,227,524 | A | 7/1993 | Jones |
| 5,233,099 | A | 8/1993 | Tabata et al. |
| 5,237,108 | A | 8/1993 | Marraccini et al. |
| 5,250,271 | A | 10/1993 | Horizoe et al. |
| 5,344,976 | A | 9/1994 | Jones et al. |
| 5,416,237 | A | 5/1995 | Aubigne et al. |
| 5,449,440 | A | 9/1995 | Rescalli et al. |
| 5,565,068 | A | 10/1996 | Parker et al. |
| RE35,377 | E | 11/1996 | Steinberg et al. |
| 5,599,976 | A | 2/1997 | Scates et al. |
| 5,770,770 | A | 6/1998 | Kim et al. |

(Continued)

FOREIGN PATENT DOCUMENTS

| EP | 0685445 | 12/1995 |
| EP | 2186787 | 5/2010 |
| WO | WO 83/03409 | 10/1983 |
| WO | WO 2008/135192 | 11/2008 |
| WO | WO 2009/009320 | 1/2009 |
| WO | WO 2009/009322 | 1/2009 |
| WO | WO 2009/009323 | 1/2009 |
| WO | WO 2009/048335 | 4/2009 |
| WO | WO 2009/063176 | 5/2009 |
| WO | WO2009/063176 A1 * | 5/2009 |
| WO | WO 2009/105860 | 9/2009 |
| WO | WO 2010/055285 | 5/2010 |

OTHER PUBLICATIONS

International Preliminary Report on Patentability for PCT/US2011/035560 mailed Aug. 27, 2012.

International Search Report and Written Opinion mailed Sep. 16, 2011 in corresponding International Application No. PCT/US2011/035560 filed May 6, 2011.

*Primary Examiner* — Sikarl Witherspoon (57) ABSTRACT

A method of removing impurities, such as halogens, sulfurs, and corrosion metal impurities, in an ethanol production process. Ion exchange resins may be used to remove these impurities from acetic acid feed streams and recycle streams that comprise unreacted acetic acid.

27 Claims, 3 Drawing Sheets

(56) References Cited

U.S. PATENT DOCUMENTS

| | | |
|---|---|---|
| 5,801,279 A | 9/1998 | Miura et al. |
| 5,821,111 A | 10/1998 | Grady et al. |
| 6,121,498 A | 9/2000 | Tustin et al. |
| 6,143,930 A | 11/2000 | Singh et al. |
| 6,225,498 B1 | 5/2001 | Blay et al. |
| 6,232,352 B1 | 5/2001 | Vidalin et al. |
| 6,294,703 B1 | 9/2001 | Hara et al. |
| 6,326,515 B1 | 12/2001 | Clode et al. |
| 6,375,807 B1 | 4/2002 | Nieuwoudt et al. |
| 6,509,180 B1 | 1/2003 | Verser et al. |
| 6,627,770 B1 | 9/2003 | Cheung et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,723,886 B2 | 4/2004 | Allison et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,115,772 B2 | 10/2006 | Picard et al. |
| 7,208,624 B2 | 4/2007 | Scates et al. |
| 7,297,236 B1 | 11/2007 | Vander Griend et al. |
| 7,351,559 B2 | 4/2008 | Verser et al. |
| 7,399,892 B2 | 7/2008 | Rix et al. |
| 7,507,562 B2 | 3/2009 | Verser et al. |
| 7,553,397 B1 | 6/2009 | Colley et al. |
| 7,572,353 B1 | 8/2009 | Vander et al. |
| 7,601,865 B2 | 10/2009 | Verser et al. |
| 7,608,744 B1 | 10/2009 | Johnston et al. |
| 7,682,812 B2 | 3/2010 | Verser et al. |
| 7,732,173 B2 | 6/2010 | Mairal et al. |
| 7,863,489 B2 | 1/2011 | Johnston et al. |
| 7,884,253 B2 | 2/2011 | Stites et al. |
| 7,888,082 B2 | 2/2011 | Verser et al. |
| 2006/0019360 A1 | 1/2006 | Verser et al. |
| 2007/0270511 A1 | 11/2007 | Melnichuk et al. |
| 2008/0135396 A1 | 6/2008 | Blum |
| 2008/0193989 A1 | 8/2008 | Verser et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0166172 A1 | 7/2009 | Casey et al. |
| 2009/0281354 A1 | 11/2009 | Mariansky et al. |
| 2009/0318573 A1 | 12/2009 | Stites et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0197485 A1 | 8/2010 | Johnston et al. |

* cited by examiner

ALCOHOL PRODUCTION PROCESS WITH IMPURITY REMOVAL

CROSS REFERENCE TO RELATED APPLICATIONS

This application claims priority to U.S. Provisional App. No. 61/332,696, filed on May 7, 2010, the entirety of which is incorporated herein by reference.

FIELD OF THE INVENTION

The present invention relates generally to processes for removing halogen and/or corrosive metal impurities from one or more streams that are directed to a hydrogenation reactor. The processes are particularly suited for removing halogen and/or corrosive metal impurities from streams, such as one or more feed or recycle streams, that are fed to a reactor for hydrogenating acetic acid to ethanol.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of acetic acid and/or other carbonyl group-containing compounds has been widely studied, and a variety of combinations of catalysts, supports, and operating conditions have been mentioned in the literature. Depending largely on manufacturing method, different commercially available acetic acid compositions contain differing levels and types of impurities. The presence of these impurities may negatively impact catalyst performance and lifetime in the catalytic reduction of acetic acid to ethanol.

In addition, the corrosive nature of acetic acid, particularly in liquid form, may cause the leaching of corrosion metals from processing conduits, reactors, and other vessels in reaction systems involving acetic acid. Such metals may also detrimentally impact catalyst performance and lifetime in reaction systems employing acetic acid, necessitating the lining of such engineering equipment with materials resistant to metal leaching and resulting in significant capital cost.

For the foregoing reasons, the need exists for new and improved processes for removing impurities from acetic acid, and in particular to removing impurities from acetic acid that is used in reaction systems for catalytically reducing acetic acid to form salable ethanol.

The need remains for ethanol production processes for removing impurities within the hydrogenation system.

SUMMARY OF THE INVENTION

In a first embodiment, the present invention is directed to a process for producing ethanol, comprising contacting a bulk acetic acid stream with an ion exchange resin to form a purified acetic acid feed stream, hydrogenating acetic acid in the purified acetic acid feed stream in the presence of a catalyst to form a crude ethanol product, separating at least a portion of the crude ethanol product in a first column into a first distillate comprising ethanol and ethyl acetate, and a first residue comprising acetic acid, and recovering ethanol from the first distillate. In one aspect, the process may involve separating at least a portion of the first distillate in a second column into a second distillate comprising ethyl acetate and a second residue comprising ethanol.

In a second embodiment, the present invention is directed to a process for producing ethanol, comprising contacting a bulk acetic acid stream with an ion exchange resin to form a purified acetic acid feed stream, hydrogenating acetic acid in the purified acetic acid feed stream in the presence of a catalyst to form a crude ethanol product, and separating at least a portion of the crude ethanol product in one or more separation units to recover an ethanol product stream having less than 500 wppb halogen and/or sulfur impurities.

In a third embodiment, the present invention is directed to a process for producing ethanol, comprising hydrogenating acetic acid from an acetic acid feed stream in a reactor in the presence of a catalyst to form a crude ethanol product, separating at least a portion of the crude ethanol product in one or more separation units to recover an ethanol product stream and an unreacted acetic acid stream, contacting a stream comprising acetic acid and at least one corrosion metal impurity with an ion exchange resin, and directing an outflow stream from the ion exchange resin to the reactor, wherein the outflow stream comprises a reduced concentration of corrosion metal impurities. The stream comprising acetic acid may be either the acetic acid feed stream and/or unreacted acetic acid stream.

In a fourth embodiment, the present invention is directed to a process for producing ethanol, comprising hydrogenating acetic acid in a reactor in the presence of a catalyst to form a crude ethanol product, separating at least a portion of the crude ethanol product in one or more separation units to recover an ethanol product stream and an unreacted acetic acid stream, contacting at least a portion of the unreacted acetic acid stream with an ion exchange resin, and recycling an outflow stream from the ion exchange resin to the reactor, wherein the outflow stream comprises a reduced concentration of corrosion metal impurities.

BRIEF DESCRIPTION OF DRAWINGS

The invention is described in detail below with reference to the appended drawings, wherein like numerals designate similar parts.

DETAILED DESCRIPTION OF THE INVENTION

Introduction

The present invention relates to processes for recovering ethanol produced by hydrogenating acetic acid in the presence of a catalyst to produce a crude ethanol product. Depending on the source of the acetic acid, the acetic acid feed stream may include one or more halogen impurities, in particular iodide and compounds thereof, and/or sulfur compounds. The acetic acid feed stream may also comprise metal contaminants, such as chromium, rhodium, iridium, platinum, iron, nickel, and/or palladium. The presence of halogen and/or sulfur impurities, even in very low levels such as less than 100 wppm, may be harmful to the hydrogenation catalyst resulting in loss of catalytic function. In addition, removing halogen and/or sulfur impurities from the hydrogenation process, even if not harmful to the particular type of catalyst, also advantageously reduces the concentration of such impurities in the final ethanol product that is ultimately recovered from the crude ethanol product. Embodiments of the present invention include a resin bed, e.g., a guard bed, to remove halogen and/or sulfur impurities from the acetic acid feed stream prior to entering the hydrogenation reactor.

In addition, during the purification of the crude ethanol product, several streams may be recycled to the reactor, in particular streams that contain unreacted acetic acid. The recycling of these streams often causes various impurities, e.g., metal contaminants and/or corrosion metals, to build up in the hydrogenation reactor over an extended period of time in continuous operations. Also the impurities may be entrained in the process stream causing fouling. Corrosion metal impurities, such as compounds containing iron, nickel, molybdenum, chromium, copper, and the like are some examples of these impurities. These corrosion metal contaminants are formed due to the corrosive nature of the acetic acid in the recycled streams. As the corrosion metal impurities are recycled to the hydrogenation reactor, these impurities may build up in sufficient quantities that they may interfere with the hydrogenation reaction and/or accelerate competing side reactions. In some embodiments, the present invention includes a resin bed to remove corrosion metal impurities from one or more recycle streams comprising acetic acid.

In some embodiments, the hydrogenation production and ethanol recovery process includes one or more resin beds for removing halogens, sulfurs, metal contaminants, and/or corrosion metal impurities. When removing two or more of the halogens, sulfurs, metal contaminants, and/or corrosion metal impurities, the process of the present invention may use separate resin beds.

Resins

The resin beds may include any type of ion exchange resin known in the art. The resins used in the present invention may include metal exchanged functional groups as described in U.S. Pat. Nos. 5,220,558 and 4,615,806, the entireties of which are hereby incorporated by reference. For example, ion exchange resins or other suitable substrates may be prepared for use in connection with the present invention by exchanging anywhere from about 1 to about 99 percent of the active sites of the resin to the silver, palladium, or mercury form by contacting the resin with a silver, palladium, or mercury salt. The silver form, e.g., silver functionalized, is particular preferred for the removal of halogen contaminants. In some embodiments, the ion exchange resin is functionalized with a co-precipitate to the impurity contained in the stream. The metal loading on the resin may vary, and preferably at least 1% of the active sites are occupied, and more preferably from 10 to 90% of the active sites, e.g., 30 to 70%. See, for example, U.S. Pat. No. 6,225,498, the entirety of which is incorporated herein by reference, which discloses methods of removing organic iodides from non-aqueous organic media comprising contacting the organic media with a silver or mercury exchanged cationic ion exchange substrate at a temperature greater than about 50° C. See also U.S. Pat. Nos. 5,801,279; 5,416,237; 5,227,524; and 5,139,981; and EP0685445, the entireties of which are incorporated herein by reference.

The resins useful for removing halogens and/or corrosion metal impurities from the process streams according to the present invention may include cation exchange resins either of the strong-acid or the weak-acid type. Both strong- and weak-acid type resins are readily available as commercial products. The weak-acid cation exchange resins are mostly copolymers of acrylic or methacrylic acids or esters or the corresponding nitriles, but a few of those marketed are phenolic resins. Preferably, strong-acid cation exchange resins are utilized. Strong-acid cation exchange resins predominantly comprise sulfonated styrene-divinylbenzene copolymers although some of the available resins of this type are phenol-formaldehyde condensation polymers. Amberlyst™ 15, Amberlite™ GT73, and Duolite ES 465 (Rohm and Haas) are exemplary commercial resins. The degree of cross linking in the styrene-divinylbenzene copolymers may vary and generally is from about 4% to 12%, preferably about 6 to 10%.

Either a gel type resin or a macroreticular type resin may be suitable, but the latter is preferred since organic components are present in the fresh acetic acid feed streams and recycled streams comprising acetic acid. Macroreticular resins are commonly employed in the catalytic art and require minimal water to maintain their swelling properties.

Other suitable guard bed materials are known in the art and include, for example, carbon, silica, alumina, ceramics, or combinations thereof. Ion exchange substrates comprising zeolites may also be employed, provided that the material is stable at the conditions of interest; that is, so long as the material will not chemically decompose or release silver or mercury in unacceptable amounts.

The halogen, sulfur, and/or corrosion metal impurity removal may be performed at temperatures ranging from 0° C. to 120° C., e.g., from 20° C. to 90° C. Lower or higher temperatures are limited only by the stability of the resin to be employed. For some types of corrosion metals, such as chromium, removal may be more efficient at the higher temperatures. At the higher temperatures, a nitrogen or CO purge may be desirable.

The processes of the present invention may be carried out in any suitable resin bed configuration. The flow rates of acetic acid feed streams or recycle stream may vary, but generally the flow through the resin bed may be from about 0.5 to about 50 bed volumes per hour (BV/hr), e.g., from about 1 to about 30 BV/hr. A bed volume is simply the volume of the resin bed.

Guard Bed

Figure 1:
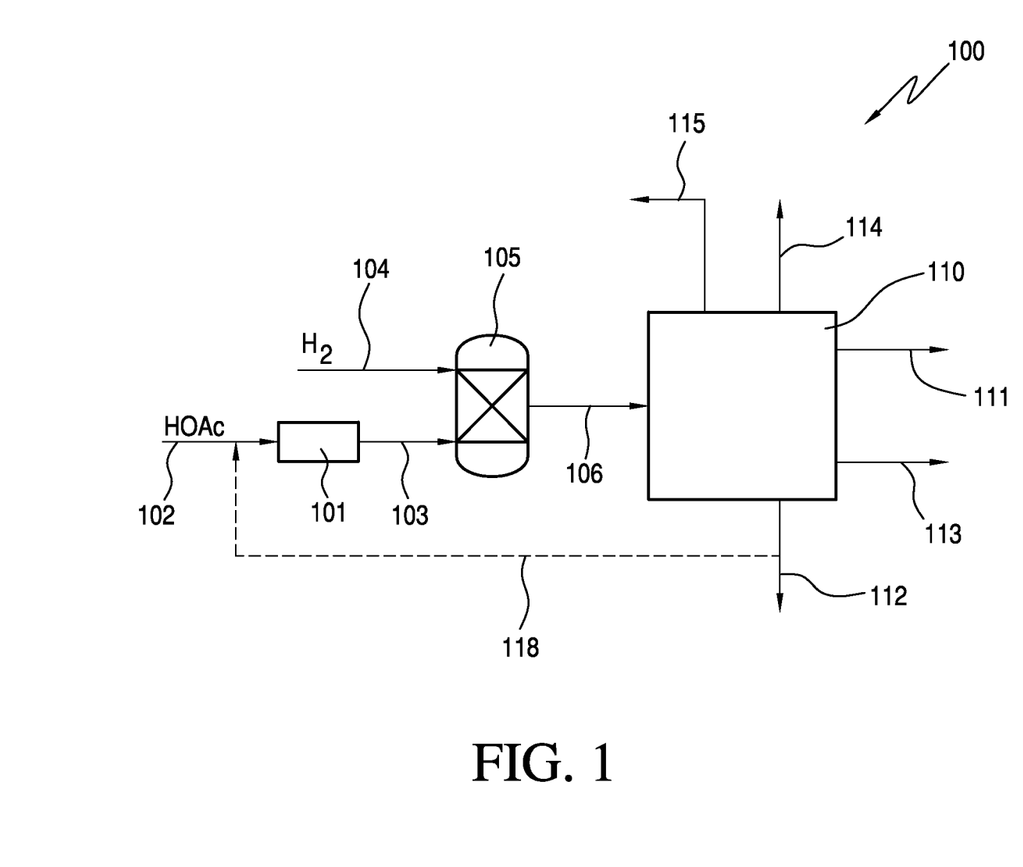
FIG. 1 is a schematic diagram of an exemplary hydrogenation system having a guard bed to remove impurities from a acetic acid feed stream in accordance with one embodiment of the present invention.

FIG. 1 is an exemplary schematic of a system 100 that includes a guard bed 101. As shown in FIG. 1, bulk acetic acid stream 102 is fed to guard bed 101. Bulk acetic acid stream 102 is in the liquid state and may be preheated before entering guard bed 101. In addition to acetic acid, the bulk acetic acid stream 102 may comprise less than 1000 wppm halogen impurities, and more preferably less than 500 wppm halogen impurities. In terms of ranges, bulk acetic acid stream 102 may comprise from 0.1 wppm to 1000 wppm halogen impurities, e.g., from 1 wppm to 500 wppm or from 10 wppm to 100 wppm. The halogen impurities may include chlorides, iodides, alkyl chlorides, and alkyl iodides such as, but not limited to, methyl iodide, ethyl iodide, hexyl iodide, methyl chloride, ethyl chloride, hexyl chloride, and mixtures thereof. The bulk acetic acid stream 102 may also comprise from 0.1 wppm to 1000 wppm sulfur impurities and/or metal contaminants, e.g., from 1 wppm to 500 wppm or from 10 wppm to 100 wppm. The amounts of halogen and sulfur impurities and metal contaminants may vary depending on the source of acetic acid. In some embodiments, the acetic acid may contain more halogen and sulfur impurities and metal contaminants.

In some embodiments, in addition to the acetic acid there may also be one or more compounds selected from the group consisting of acetic anhydride, acetaldehyde, ethyl acetate, propanoic acid, and mixtures thereof. Water may also be present, in low amounts, in the bulk acetic acid feed 102. In some embodiment, bulk acetic acid feed 102 may comprise water in amounts greater than 0.15 wt. %.

Guard bed 101 contains a suitable resin as described above, and preferably removes substantially all of the halogen impurities in the bulk acetic acid stream 102 to produce a purified acetic acid feed stream 103. The concentration of halogen impurities in purified acetic acid feed stream 103 may vary, but generally is from 5 wppb to 500 wppb, e.g., 10 wppb to 100 wppb. Concentrations below 5 wppb may be achievable depending on the type of resin employed, but generally amounts of less than 500 wppb are sufficient to prevent a loss of catalytic function in the hydrogenation reactor.

In addition, guard bed 101 may also contain a suitable resin to remove substantially all of the sulfur impurities and/or metal contaminants in the bulk acetic acid stream 102 to produce a purified acetic acid feed stream 103. The concentration of sulfur impurities and/or metal contaminants in purified acetic acid feed stream 103 may vary, but generally is from 5 wppb to 500 wppb, e.g., 10 wppb to 100 wppb. Concentrations below 5 wppb may be achievable depending on the type of resin employed, but generally amounts of less than 500 wppb are sufficient to prevent a loss of catalytic function in the hydrogenation reactor.

The purified acetic acid stream 103 is fed along with hydrogen 104 to hydrogenation reactor 105 to produce a crude product 106. In one embodiment, hydrogenation reactor 105 may be constructed of stainless steel or carbon steel. In some embodiments, reactor 105 may not be lined. Although higher grader of materials may be used, the present invention preferably removes the halogen and sulfur impurities and metal contaminants, and thus reduces the need for a higher grade of material. Crude product 106 is fed to separation section 110 to recover an ethanol product stream 111 and separate one or more other streams. Separation section 110 comprises one or more columns, flashers, membranes, and/or adsorption units. Separation section 110 may also remove unreacted acetic acid in stream 112 when the conversion is not complete, water stream 113, any organic or light components 114 formed during acetic acid hydrogenation, and/or non-condensable gases 115.

One or more of streams 112, 113, 114, and/or 115 may be returned to reactor 105. Optionally, a portion of stream 112 may also be fed to guard bed 101 via optional stream 118 before being returned to reactor 105. Optional stream 118 may comprise trace impurities, e.g., in amounts of less than 100 wppm, including halogen impurities, corrosion metal impurities, and organic impurities such as acetaldehyde and acetone. Guard bed 101 advantageously removes these impurities to prevent a build up of the impurities that may impact the catalytic function.

Guard bed 101 may also reduce halogen impurities so that the recovered ethanol product is substantially free of halogen impurities. In one embodiment, ethanol product stream 111 comprises less than 500 wppb halogen and/or sulfur impurities, e.g., less than 100 wppb halogen impurities or less than 50 wppb halogen and/or sulfur impurities. This may reduce the need for post-recovery processing of ethanol product stream 111.

Corrosion Metal Removal

Figure 2:
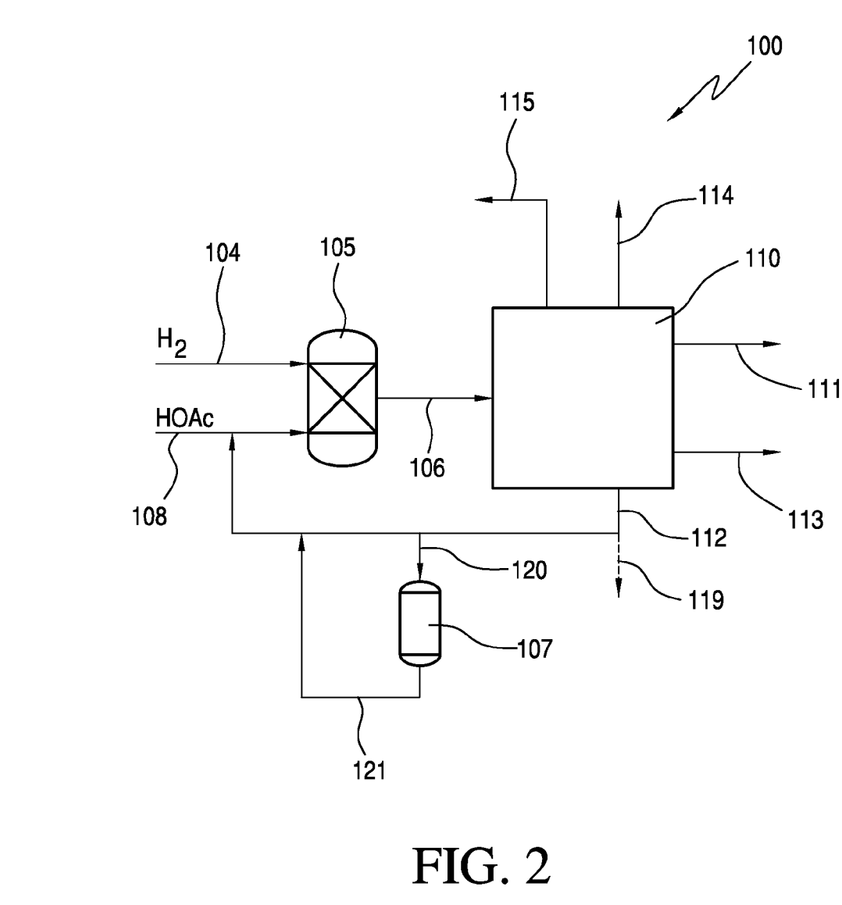
FIG. 2 is a schematic diagram of an exemplary hydrogenation system having a resin bed to remove corrosion metals from a recycled acetic acid stream in accordance with one embodiment of the present invention.

FIG. 2 is an exemplary schematic of a system 100 that includes a resin bed 107 for removing corrosion metals from stream 120, which comprises unreacted acetic acid. Acetic acid feed stream 108 and hydrogen feed stream 104 are fed to reactor 105. Optionally, acetic acid feed stream 108 may pass through one or more guard beds as described above in FIG. 1. Reactor 105 produces a crude ethanol product 106 that is separated in separation section 110. In addition to ethanol product stream 111, a stream 112 comprising unreacted acetic acid is withdrawn from separation section 110 and returned to reactor 105. Optionally, a portion of stream 112 may be purged as indicated by optional line 119. Over continuous operation, corrosion metals may build up in stream 112 due to the corrosive nature of the acetic acid contained therein. These corrosion metals may cause fouling of the processing equipment. In one embodiment, stream 112 comprises corrosion metal impurities in an amount from 0.025 wt. % to 1.0 wt. %, based on the total weight of stream 112, e.g., from 0.025 wt. % to 0.5 wt. % or from 0.025 to 0.1 wt. %. As shown, a slipstream 120 is taken from stream 112 and fed to a resin bed 107. Depending on the reaction conditions, the amount of stream 112 directed to resin bed 107 via slipstream 120 may be from 0.1 to 10% of the total mass flow of stream 112, and more preferably about 1%. Resin bed 107 comprises a suitable resin as described above for removing corrosion metals.

Resin bed 107 may reduce the concentration of corrosion metal impurities to very low levels. Outflow stream 121 from resin bed 107 preferably comprises unreacted acetic acid and a concentration of corrosion metal impurities that is less than 500 wppb, e.g., less than 100 wppb or less than 50 wppb. Outflow stream 121 may be combined with stream 112 and co-fed with acetic acid feed stream 108 to reactor 105.

In some embodiments, it may be advantageous to also provide an aqueous stream to resin bed 107 to further remove corrosion metals. Water stream 113, or more preferably a portion thereof such as from 0.5% to 50%, may be fed along with stream 112 to resin bed. When water stream 113 is fed, it may be necessary to subsequently remove the water from outflow stream 121 using a weak acid recovery system or one or more membranes to prevent larger volumes of water from being returned to reactor 105.

Acetic Acid Hydrogenation

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

As indicated above, the bulk acetic acid may also comprise halogen impurities, which may be removed by the guard beds of the present invention. The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

In one embodiment, after removing the halogen impurities, the acetic acid may be vaporized at the reaction temperature. The resulting vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal, or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. Most preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another, or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from both the first and second metals. In preferred embodiments, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal is preferably from 0.05 to 4 wt. %, e.g., from 0.1 to 3 wt. %, or from 0.1 to 2 wt. %.

In addition to one or more metals, in some embodiments of the present invention, the catalyst further comprises a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $CO_2O_3$, and $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. The basic support modifier may be selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain N or Pro. The Saint-Gobain N or Pro SS61138 silica exhibits the following properties: contains approximately 95 wt. % high surface area silica; surface area of about 250 $m^2/g$; median pore diameter of about 12 nm; average pore volume of about 1.0 $cm^3/g$ as measured by mercury intrusion porosimetry; and packing density of about 0.352 $g/cm^3$ (22 $lb/ft^3$).

Another preferred silica support material is KA-160 silica spheres from Süd-Chemie having a nominal diameter of about 5 mm, a density of about 0.562 g/ml, an absorptivity of about 0.583 g $H_2O$/g support, a surface area of about 160 to 175 $m^2/g$, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments, a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 40 wt. % water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0 to 90 | 0 to 50 | 15 to 70 | 20 to 70 |
| Water | 5 to 40 | 5 to 30 | 10 to 30 | 10 to 26 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product comprises acetic acid in an amount less than 20 wt. %, e.g., less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

When a guard bed is used, the amount of halogen impurities in crude ethanol product may be less than 500 wppb. Higher levels of halogen impurities may be expected without a guard bed and would depend on the concentration of halogen impurities in the feed. In addition, the amount of corrosion metal impurities in the crude ethanol product may be less than 500 wppb when a resin bed is used to remove such impurities.

Ethanol Recovery

Figure 3:
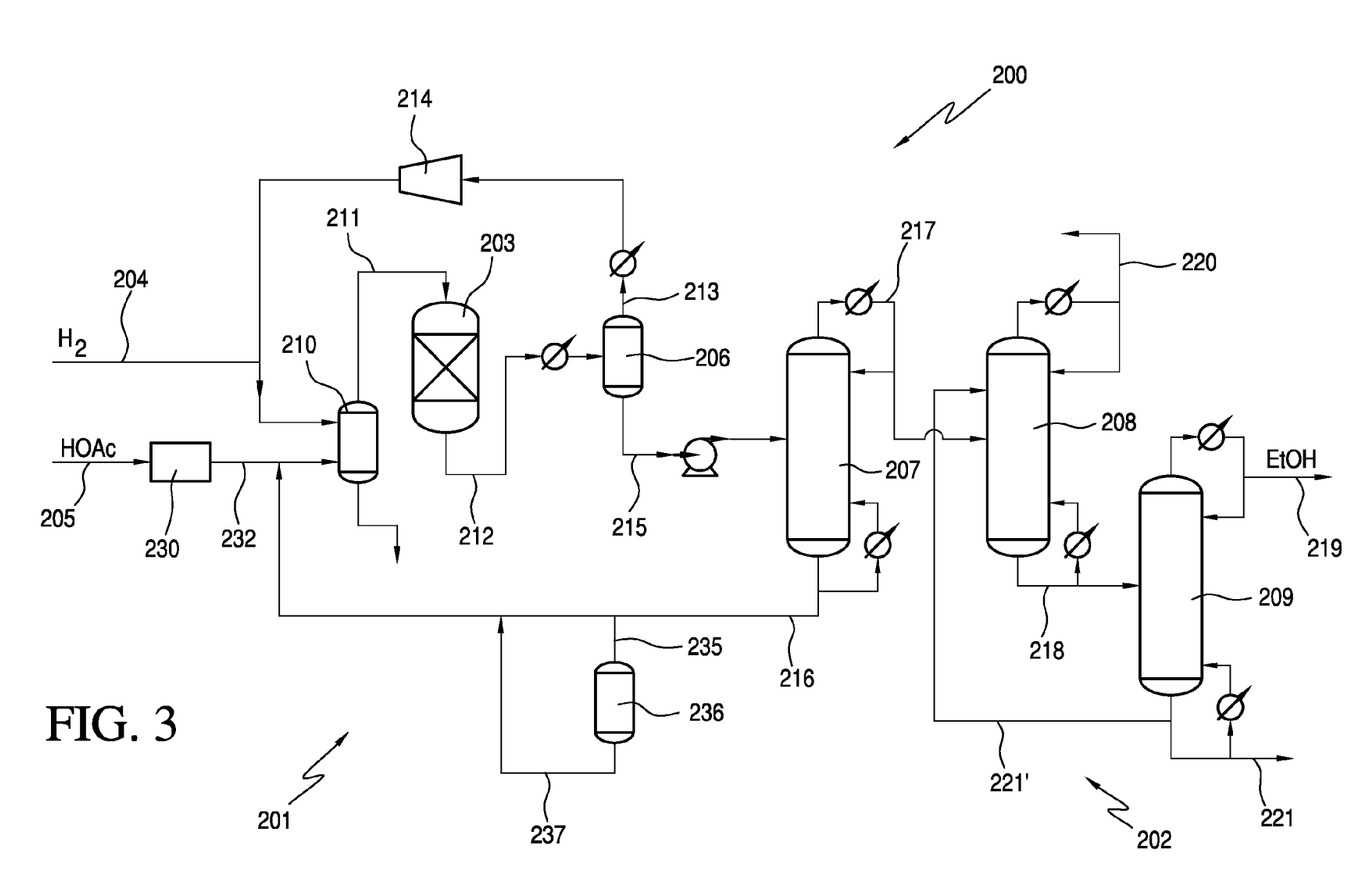
FIG. 3 is a schematic diagram of an exemplary hydrogenation system having a guard bed and a resin bed for removing corrosion metals in accordance with another embodiment of the present invention.

The crude ethanol product may be treated as shown by an exemplary hydrogenation system 200 in FIG. 3. System 200 comprises reaction zone 201 and distillation zone 202.

Bulk acetic acid stream 205 is fed to guard bed 230 to produce purified acetic acid feed line 232 as described above in FIG. 1. Purified acetic acid feed line 232 contains less halogen impurities than bulk acetic acid 205, and may comprise less than 500 wppb halogen impurities.

Hydrogen and purified acetic acid are fed to a vaporizer 210 via lines 204 and 232, respectively, to create a vapor feed stream in line 211 that is directed to reactor 203. In one embodiment, lines 204 and 232 may be combined and jointly fed to the vaporizer 210. The temperature of the vapor feed stream in line 211 is preferably from 100° C. to 350° C., e.g., from 120° C. to 310° C. or from 150° C. to 300° C. Any feed that is not vaporized is removed from vaporizer 210, as shown in FIG. 3, and may be recycled or discarded. In one embodiment the blowdown stream from vaporizer 210 may comprise halogen and/or sulfur impurities. In addition, although FIG. 3 shows line 211 being directed to the top of reactor 203, line 211 may be directed to the side, upper portion, or bottom of reactor 203. Further modifications and additional components to reaction zone 201 are described below.

Reactor 203 contains the catalyst that is used in the hydrogenation of the carboxylic acid, preferably acetic acid. During the hydrogenation process, a crude ethanol product is withdrawn, preferably continuously, from reactor 203 via line 212.

The crude ethanol product may be condensed and fed to flasher 206, which, in turn, provides a vapor stream and a liquid stream. The flasher 206 may operate at a temperature of from 20° C. to 250° C., e.g., from 30° C. to 225° C. or from 60° C. to 200° C. The pressure of flasher 206 may be from 50 kPa to 2000 kPa, e.g., from 75 kPa to 1500 kPa or from 100 to 1000 kPa.

The vapor stream 213 exiting flasher 206 may comprise hydrogen and hydrocarbons, and may be purged and/or returned to reaction zone 201. As shown, vapor stream 213 is combined with the hydrogen feed 204 and co-fed to vaporizer 210. In some embodiments, the returned vapor stream 213 may be compressed using compressor 214 before being combined with hydrogen feed 204.

The liquid stream 215 from flasher 206 is withdrawn and further separated to recover ethanol. Although various embodiments of the present invention may use different separation systems, it is preferred to withdraw at least one stream comprising unreacted acetic acid. As shown in FIG. 3, liquid stream 215 is pumped as a feed composition to the side of first column 207, also referred to as an "acid separation column" The contents of line 215 typically will be substantially similar to the product obtained directly from the reactor 203, and may, in fact, also be characterized as a crude ethanol product. However, liquid stream 215 preferably has substantially no hydrogen, carbon dioxide, methane or ethane, which are removed by flasher 206. Exemplary compositions of line 215 are provided in Table 2. It should be understood that liquid stream 215 may contain other components, not listed, such as additional components in the feed.

TABLE 2

FEED COMPOSITION

| | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 15 to 70 |
| Water | 5 to 35 | 5 to 30 | 10 to 30 |
| Ethyl Acetate | <20 | 0.001 to 15 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| $C_3$+ Alcohols | <8 | <0.1 | <0.05 |
| Other Esters | <5 | <0.005 | <0.001 |
| Other Ethers | <5 | <0.005 | <0.001 |

The amounts indicated as less than (<) in the tables throughout present specification are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the liquid stream 215 may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

Optionally, the crude ethanol product may pass through one or more membranes to separate hydrogen and/or other non-condensable gases. In other optional embodiments, the crude ethanol product may be fed directly to the acid separation column as a vapor feed and the non-condensable gases may be recovered from the overhead of the column.

When the content of acetic acid in line 215 is less than 5 wt. %, the acid separation column 207 may be skipped and line 215 may be introduced directly to second column 208, also referred to herein as a "light ends column" In addition, column 207 may be operated to initially remove a substantial portion of water as the residue.

In the embodiment shown in FIG. 3, line 215 is introduced in the lower part of first column 207, e.g., lower half or lower third. Depending on the acetic acid conversion and operation of column 207, unreacted acetic acid, water, and other heavy components, if present, are removed from the composition in line 215 and are withdrawn, preferably continuously, as residue. In some embodiments, especially with higher conversions of acetic acid of at least 80%, or at least 90%, it may be beneficial to remove a majority of water in line 215 along with substantially all the acetic acid in residue stream 216. Residue stream 216 may be recycled to reaction zone 201. In addition, a portion of the water in residue stream 216 may be separated and purged with the acid rich portion being returned to reaction zone 201.

FIG. 3 also includes a resin bed 236 for removing corrosion metal impurities from residue stream 216. Preferably, a portion of the residue stream 216 that is rich in acetic acid is fed to resin bed 236 via line 235 as described above in FIG. 2. The amount of corrosion metal impurities in the outflow stream 237 of residue bed 236 may be less than 500 wppb, e.g., less than 100 wppb or less than 50 wppb.

In other embodiments, the residue stream 216 may be a dilute acid stream that may be treated in a weak acid recovery system or sent to a reactive distillation column to convert the acid to esters.

First column 207 also forms an overhead distillate, which is withdrawn in line 217, and which may be condensed and refluxed, for example, at a ratio of from 10:1 to 1:10, e.g., from 3:1 to 1:3 or from 1:2 to 2:1.

The columns shown in FIG. 3 may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section and so on.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

When first column 207 is operated under standard atmospheric pressure, the temperature of the residue exiting in line 216 from column 207 preferably is from 95° C. to 120° C., e.g., from 105° C. to 117° C. or from 110° C. to 115° C. The temperature of the distillate exiting in line 217 from column 207 preferably is from 70° C. to 110° C., e.g., from 75° C. to 95° C. or from 80° C. to 90° C. In some embodiments, the pressure of first column 207 may range from 0.1 kPa to 510 kPa, e.g., from 1 kPa to 475 kPa or from 1 kPa to 375 kPa. In one exemplary embodiment a distillate and residue compositions for first column 207 are provided in Table 3 below. Note that these compositions may change depending on acetic acid conversion, the operation of the column and whether a majority of the water is removed in the residue. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

| FIRST COLUMN | | | |
|---|---|---|---|
| | Conc. (wt. %) | Conc. (wt. %) | Conc. (wt. %) |
| Distillate | | | |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue | | | |
| Acetic Acid | 60 to 100 | 70 to 95 | 85 to 92 |
| Water | <30 | 1 to 20 | 1 to 15 |
| Ethanol | <1 | <0.9 | <0.07 |

Some species, such as acetals, may decompose in column 207 to low or even undetectable amounts. In addition, an equilibrium reaction between acetic acid/ethanol and ethyl acetate may occur in the crude ethanol product after it exits reactor 203. Depending on the concentration of acetic acid in the crude ethanol product, this equilibrium may be driven toward formation of ethyl acetate. This reaction may be regulated using the residence time and/or temperature of crude ethanol product.

The distillate, e.g., overhead stream, of first column 207 optionally is condensed and refluxed as shown in FIG. 3, preferably, at a reflux ratio of 1:5 to 10:1. The distillate in line 217 preferably comprises ethanol, ethyl acetate, and water, along with other impuritie.

The first distillate in line 217 is introduced to the second column 208, also referred to as the "light ends column," preferably in the top part of column 208, e.g., top half or top third. Second column 208 may be a tray column or packed column. In one embodiment, second column 208 is a tray column having from 5 to 70 trays, e.g., from 15 to 50 trays or from 20 to 45 trays. As one example, when a 30 tray column is utilized in a column without water extraction, line 217 is introduced at tray 2. In one embodiment, the second column 208 may be an extractive distillation column. In such embodiments, an extraction agent, such as water, may be added to second column 208. If the extraction agent comprises water, it may be obtained from an external source or from an internal return/recycle line from one or more of the other columns.

In some embodiments, a portion of the water in first distillate 217 may be removed prior to entering second column 208, using one or more membranes, and/or adsorptions units.

Although the temperature and pressure of second column 208 may vary, when at about 20 kPa to 70 kPa, the temperature of the second residue exiting in line 218 from second column 208 preferably is from 30° C. to 75° C., e.g., from 35° C. to 70° C. or from 40° C. to 65° C. The temperature of the second distillate exiting in line 220 from second column 208 preferably is from 20° C. to 55° C., e.g., from 25° C. to 50° C. or from 30° C. to 45° C. Column 208 may operate at a reduced pressure, near or at vacuum conditions, to further favor separation of ethyl acetate and ethanol. In other embodiments, the pressure of second column 208 may range from 0.1 kPa to 510 kPa, e.g., from 1 kPa to 475 kPa or from 1 kPa to 375 kPa. Exemplary components for the distillate and residue compositions for second column 208 are provided in Table 4 below. It should be understood that the distillate and residue may also contain other components, not listed, such as components in the feed.

TABLE 4

SECOND COLUMN

|  | Conc. (wt. %) | Conc. (wt. %) | Conc. (wt. %) |
|---|---|---|---|
| Distillate |  |  |  |
| Ethyl Acetate | 10 to 90 | 25 to 90 | 50 to 90 |
| Acetaldehyde | 1 to 25 | 1 to 15 | 1 to 8 |
| Water | 1 to 25 | 1 to 20 | 4 to 16 |
| Ethanol | <30 | 0.001 to 15 | 0.01 to 5 |
| Acetal | <5 | 0.001 to 2 | 0.01 to 1 |
| Residue |  |  |  |
| Water | 5 to 70 | 30 to 60 | 30 to 50 |
| Ethanol | 20 to 95 | 30 to 70 | 40 to 70 |
| Ethyl Acetate | <3 | 0.001 to 2 | 0.001 to 0.5 |
| Acetic Acid | <0.5 | 0.001 to 0.3 | 0.001 to 0.2 |

The weight ratio of ethanol in the second residue to ethanol in the second distillate preferably is at least 2:1, e.g., at least 5:1, at least 8:1, at least 10:1 or at least 15:1. The weight ratio of ethyl acetate in the second residue to ethyl acetate in the second distillate preferably is less than 0.4:1, e.g., less than 0.2:1 or less than 0.1:1. In embodiments that use an extractive column with water as an extraction agent as the second column 208, the weight ratio of ethyl acetate in the second residue to ethyl acetate in the second distillate is less than 0.1:1.

Returning to the second distillate, which comprises ethyl acetate and/or acetaldehyde, the second distillate preferably is refluxed as shown in FIG. 3, for example, at a reflux ratio of from 1:30 to 30:1, e.g., from 1:5 to 5:1 or from 1:3 to 3:1. In one aspect, the second distillate in line 220 or portion thereof may be returned reactor 203. In some embodiments, it may be advantageous to return a portion of second distillate to reactor 203 or in a secondary reactor. In certain embodiments and as shown in FIG. 3, the second distillate may be fed to an acetaldehyde removal column (not shown) to recover aldehyde that may be recycled to reactor 203 and purge ethyl acetate from system 200. In other embodiments, the second distillate may be hydrolyzed or fed to an hydrogenolysis reactor (not shown) to produce ethanol from ethyl acetate. In still other embodiments, the second distillate may be purged from system.

Depending on the water concentration of second residue in line 218, it may be necessary to remove at least some of the water from the second residue. As shown in FIG. 3, the second residue from the bottom of second column 208, which comprises ethanol and water, is fed via line 218 to third column 209, also referred to as a "product column." The second residue in line 218 is introduced in the lower part of third column 209, e.g., lower half or lower third. Third column 209 recovers ethanol as the distillate in line 219. The distillate 219 of third column 209 preferably is refluxed, for example, at a reflux ratio of from 1:10 to 10:1, e.g., from 1:3 to 3:1 or from 1:2 to 2:1.

In preferred embodiments, the third residue in line 221, which preferably comprises primarily water, is removed from the system 200. Optionally, the third residue 221 may be partially returned to any portion of the system 200. For example, as shown in FIG. 3, a portion of the third residue in line 221 may be taken via line 221' and returned to second column 208.

Third column 209 is preferably a tray column as described above and preferably operates at atmospheric pressure. The temperature of the third distillate exiting in line 219 from third column 209 preferably is from 60° C. to 110° C., e.g., from 70° C. to 100° C. or from 75° C. to 95° C. The temperature of the third residue exiting from third column 209 in line 221 preferably is from 70° C. to 115° C., e.g., from 80° C. to 110° C. or from 85° C. to 105° C., when column 209 is operated at atmospheric pressure. Exemplary distillate compositions and residue compositions for third column 109 are provided in Table 5 below.

TABLE 5

THIRD COLUMN

|  | Conc. (wt. %) | Conc. (wt. %) | Conc. (wt. %) |
|---|---|---|---|
| Distillate |  |  |  |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue |  |  |  |
| Water | 75 to 100 | 80 to 100 | 90 to 100 |
| Ethanol | <0.8 | 0.001 to 0.5 | 0.005 to 0.05 |

TABLE 5-continued

THIRD COLUMN

| | Conc. (wt. %) | Conc. (wt. %) | Conc. (wt. %) |
|---|---|---|---|
| Ethyl Acetate | <1 | 0.001 to 0.5 | 0.005 to 0.2 |
| Acetic Acid | <2 | 0.001 to 0.5 | 0.005 to 0.2 |

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In preferred embodiments, the finished ethanol composition from distillate 219 is substantially free of acetaldehyde and may comprise less than 8 wppm of acetaldehyde, e.g., less than 5 wppm or less than 1 wppm. In preferred embodiment, third distillate 219 may comprise less than 500 wppb halogen and/or sulfur impurities, e.g., less than 100 wppb or less than 50 wppb. Third distillate 219 also preferably comprises less than 500 wppb corrosion metal impurities, e.g., less than 100 wppb or less than 50 wppb.

The ethanol product may be an industrial grade ethanol preferably comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 6.

TABLE 6

FINISHED ETHANOL

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm. In one embodiment, the finished ethanol composition is substantially free of halogen impurities, optionally comprising less than 500 wppb halogen and/or sulfur impurities, e.g., less than 100 wppb or less than 50 wppb. In one preferred embodiment, the ethanol composition comprises from 5 to 50 wppb halogen impurities, more preferably from 5 to 25 or from 5 to 10 wppb.

In some embodiments, when further water separation is used, the ethanol product may be withdrawn as a stream from the water separation unit. Particularly preferred techniques include the use of a distillation column, one or more membranes, one or more adsorption units or a combination thereof. Third distillate 219 may be further purified to form an anhydrous ethanol product stream, i.e., "finished anhydrous ethanol," using one or more additional separation systems, such as, for example, distillation columns (e.g., a finishing column), membranes, adsorption units, or molecular sieves. Anhydrous ethanol may be suitable for fuel applications. In such embodiments, the ethanol concentration of the ethanol product may be higher than indicated in Table 6, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

The invention claimed is:

1. A process for producing ethanol, comprising:
    contacting a bulk acetic acid stream with an ion exchange resin to form a purified acetic acid feed stream;
    hydrogenating acetic acid in the purified acetic acid feed stream in the presence of a catalyst comprising platinum and tin on a support or cobalt and tin on a support and operating the reaction at a pressure between 50 kPa to 2300 kPa to form a crude ethanol product;

separating at least a portion of the crude ethanol product in a first column into a first distillate comprising ethanol and ethyl acetate, and a first residue comprising acetic acid; and recovering ethanol from the first distillate.

2. The process of claim 1, wherein the bulk acetic acid stream comprises less than 1000 wppm halogen and/or sulfur impurities.

3. The process of claim 1, wherein the bulk acetic acid stream comprises 0.1 wppm to 1000 wppm halogen and/or sulfur impurities.

4. The process of claim 3, wherein the purified acetic acid feed stream comprises less than 500 wppb halogen and/or sulfur impurities.

5. The process of claim 3, wherein the halogen impurities are selected from methyl iodide, ethyl iodide, hexyl iodide, methyl chloride, ethyl chloride, hexyl chloride, and mixtures thereof.

6. The process of claim 1, separating at least a portion of the first distillate in a second column into a second distillate comprising ethyl acetate and a second residue comprising ethanol.

7. The process of claim 6, further comprising recovering an ethanol product stream from the second residue.

8. The process of claim 7, wherein the ethanol product stream comprises less than 500 wppb halogen and/or sulfur impurities.

9. The process of claim 7, wherein the ethanol product stream comprises from 5 to 50 wppb halogen sulfur impurities.

10. The process of claim 1, further comprising recycling at least a portion of the first residue to the ion exchange resin.

11. The process of claim 9, wherein the first residue comprises a halogen impurity, sulfur impurity, corrosion metal impurity, organic impurity, or combination thereof.

12. The process of claim 1, wherein the ion exchange resin is a strong-acid cation exchange resin.

13. The process of claim 1, wherein the ion exchange resin is silver functionalized.

14. The process of claim 1, wherein the reactor is constructed of stainless steel or carbon steel.

15. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

16. A process for producing ethanol, comprising:
contacting a bulk acetic acid stream with an ion exchange resin to form a purified acetic acid feed stream;
hydrogenating acetic acid in the purified acetic acid feed stream in the presence of a catalyst comprising platinum and tin on a support or cobalt and tin on a support and operating the reaction at a pressure between 50 kPa to 2300 kPa to form a crude ethanol product; and
separating at least a portion of the crude ethanol product in one or more separation units to recover an ethanol product stream having less than 500 wppb halogen and/or sulfur impurities.

17. The process of claim 16, wherein the ethanol product stream is substantially free of halogen and/or sulfur impurities.

18. The process of claim 16, wherein the bulk acetic acid stream comprises less than 1000 wppm halogen and/or sulfur impurities.

19. The process of claim 16, wherein the bulk acetic acid stream comprises 0.1 wppm to 1000 wppm halogen and/or sulfur impurities.

20. The process of claim 16, wherein the purified acetic acid feed stream comprises less than 500 wppb halogen and/or sulfur impurities.

21. The process of claim 16, wherein the ion exchange resin is a strong-acid cation exchange resin.

22. The process of claim 16, wherein the ion exchange resin is silver functionalized.

23. A process for producing ethanol, comprising:
hydrogenating acetic acid from an acetic acid feed stream in a reactor in the presence of a catalyst to form a crude ethanol product;
separating at least a portion of the crude ethanol product in one or more separation units to recover an ethanol product stream and an unreacted acetic acid stream comprising corrosion metal impurities in an amount from 0.025 wt. % to 1.0 wt. %, wherein at least one of the corrosion metal impurities is selected from the group consisting of iron, nickel, molybdenum, chromium, and copper;
contacting a stream comprising acetic acid and at least one corrosion metal impurity with an ion exchange resin; and
directing an outflow stream from the ion exchange resin to the reactor, wherein the outflow stream comprises a reduced concentration of corrosion metal impurities.

24. The process of claim 23, wherein the acetic acid feed stream is contacted with the ion exchange resin.

25. The process of claim 23, wherein the unreacted acetic acid stream is contacted with the ion exchange resin.

26. The process of claim 23, wherein the outflow stream comprises less than 500 wppb corrosion metals.

27. The process of claim 23, wherein the ion exchange resin is a strong-acid cation exchange resin.

* * * * *